(12) United States Patent
Schwager et al.

(10) Patent No.: US 8,864,802 B2
(45) Date of Patent: Oct. 21, 2014

(54) IMPLANT FOR BONE FIXATION

(75) Inventors: Manuel Schwager, Zurich (CH);
Pierre-Luc Sylvestre, Grenchen (CH);
Robert Wider, Derendingen (CH)

(73) Assignee: Stryker Trauma SA (CH)

( * ) Notice: Subject to any disclaimer, the term of this patent is extended or adjusted under 35 U.S.C. 154(b) by 485 days.

(21) Appl. No.: 13/115,437

(22) Filed: May 25, 2011

(65) Prior Publication Data

US 2011/0313422 A1    Dec. 22, 2011

(30) Foreign Application Priority Data

May 25, 2010    (EP) ..................................... 10005423

(51) Int. Cl.
*A61B 17/80* (2006.01)

(52) U.S. Cl.
CPC ................................ *A61B 17/8057* (2013.01); *A61B 17/8061* (2013.01)
USPC ....................................................... 606/286

(58) Field of Classification Search
USPC ...................... 606/70, 71, 280–299
See application file for complete search history.

(56) References Cited

U.S. PATENT DOCUMENTS

| | | | |
|---|---|---|---|
| 5,601,553 A * | 2/1997 | Trebing et al. | 606/86 B |
| 6,129,730 A | 10/2000 | Bono et al. | |
| 6,322,562 B1 | 11/2001 | Wolter et al. | |
| 6,454,771 B1 | 9/2002 | Michelson | |
| 6,602,256 B1 | 8/2003 | Hayes | |
| 6,623,486 B1 * | 9/2003 | Weaver et al. | 606/281 |
| 7,137,987 B2 | 11/2006 | Patterson et al. | |
| 7,648,508 B2 | 1/2010 | Lutz et al. | |
| 7,776,076 B2 | 8/2010 | Grady, Jr. et al. | |
| 8,100,952 B2 * | 1/2012 | Matityahu | 606/280 |
| 2004/0030339 A1 | 2/2004 | Wack et al. | |
| 2005/0261688 A1 | 11/2005 | Grady et al. | |
| 2006/0004362 A1 * | 1/2006 | Patterson et al. | 606/69 |
| 2006/0095044 A1 | 5/2006 | Grady et al. | |
| 2006/0173458 A1 | 8/2006 | Forstein et al. | |
| 2007/0173836 A1 | 7/2007 | Prien | |
| 2008/0021477 A1 | 1/2008 | Strnad et al. | |
| 2008/0306550 A1 | 12/2008 | Matityahu | |
| 2010/0057138 A1 | 3/2010 | Murner et al. | |

FOREIGN PATENT DOCUMENTS

| | | |
|---|---|---|
| DE | 4343117 A1 | 6/1995 |
| EP | 0 705 572 A2 | 4/1996 |
| WO | 2004107957 A2 | 12/2004 |
| WO | 2006014391 A1 | 2/2006 |

OTHER PUBLICATIONS

Koval, et al., "Distal Femoral Fixation: A Biomechanical Comparison of the Standard Condylar Buttress Plate, a Locked Buttress Plate, and the 95-Degree Blade Plate", Jouranl of Orthopaedic Trauma, 11 (7): 521-524, Oct. 1997.

(Continued)

*Primary Examiner* — Christopher Beccia
(74) *Attorney, Agent, or Firm* — Lerner, David, Littenberg, Krumholz & Mentlik, LLP (57) ABSTRACT

An implant for use in orthopedic surgery for fixation of bone has a shaft region and a head region, both including a plurality of holes for receiving bone fasteners. The head region of the implant has a central screw hole and threaded surrounding screw holes surrounding the central screw hole in a defined configuration.

26 Claims, 9 Drawing Sheets

(56) References Cited

OTHER PUBLICATIONS

Synthes, "LCP Condylar Plate 4.5/5.0. Part LCP Periarticular Plating System.", Technique Guide, p. 3, 12, 21, 25, 22, May 2008.

United Stated Court of Appeals for the Federal Circuit, pp. 2-17, Jul. 9, 2013.

AxSOS Locking Plate System, Operative Technique, Stryker, 2008.

* cited by examiner

IMPLANT FOR BONE FIXATION

CROSS-REFERENCE TO RELATED APPLICATION

This application claims the benefit of European Patent Application No. 10005423.8 filed May 25, 2010, the disclosure of which is hereby incorporated herein by reference.

BACKGROUND OF THE INVENTION

The present disclosure generally relates to an implant such as a bone plate for use in orthopedic surgery, preferably for fixation of bone. The disclosure further relates to an implant system and a method for fracture fixation of bone.

Bone plates may be employed for treating periarticular and/or intra-articular fractures of, for example, the proximal humerus, distal femur, proximal tibia or the distal tibia. Such bone plates are available in a plurality of variations for different applications and can have an I-, T-, L-, cloverleaf- or calcaneal-shape.

Bone plates for periarticular and other fractures can include threaded and unthreaded holes to receive locking and non-locking screws, respectively. The locking screws can be secured to the bone plate, wherein a threaded head of the locking screw mates with a corresponding thread on an inner surface of a plate hole. Further, the non-locking screws (such as compression or cortical screws) are typically inserted through plate holes having an unthreaded curved or conical portion into bone for providing compression of a fracture by pushing bone fragments towards each other. The configuration of the plate holes is often crucial for the medical success of the implant.

U.S. Pat. No. 5,601,553 relates to an anterior thoracolumbar locking bone plate. The bone plate comprises a plurality of threaded screw holes which are located at both extreme ends of the plate for receiving locking screws. Further, the bone plate is provided with elongated holes with a camming surface for receiving temporary screws. A threaded central hole is arranged at a midpoint of the entire bone plate. The bone plate further comprises a curved lower surface for contacting to bone, and an upper surface having two intersecting planes which meet at a central ridge portion.

U.S. Pat. No. 7,776,076 relates to bone plates having an I-, L- or T-shape. The head portion of the bone plate includes threaded screw holes which are orientated such that the axes of the holes intersect at a point beneath the lower surface of the bone plate. Further, bone screws are threadedly engaged with the holes for rigidly anchoring the bone plate to the fractured bone.

U.S. Pat. No. 7,137,987 relates to a bone plating system for fixating distal or proximal ends of long bones. The bone plate has a T- or fork-shaped head portion. The head portion of the bone plate includes a plurality of threaded plate holes for receiving locking bone screws. Further, one or more non-threaded plate holes for receiving a non-locking cancellous bone screw are provided near the peripheral side of the head portion.

The conventional bone plate systems for fracture fixation of bone have several drawbacks. In the vicinity of a compression screw, conventional bone plates cannot guarantee a desired screw-plate-bone construct stability, since compression screws cannot be locked to unthreaded plate holes. Therefore, it is possible that the bone plate is shifted in an undesired direction or is pulled out. Further, the bone plate may lose the contact between the bone contacting surface of the plate and the bone. Thus, the medical success may decrease and rapid healing may not achieved.

BRIEF SUMMARY OF THE INVENTION

Aspects of the present disclosure are directed to facilitating a rapid healing of a bone fracture and guaranteeing a high screw-plate-bone construct stability.

According to a first aspect, there is provided an implant comprising a shaft region having one or more holes for receiving bone fasteners, and a head region extending from the shaft region and having a plurality of circular holes for receiving bone fasteners. Bone fasteners can, for example, include locking screws, non-locking screws such as compression or cortical screws, and bone pegs having rod-like or pin-like shafts. Further, the plurality of circular holes includes an unthreaded central screw hole having a center and at least three locking screw holes each having a center and surrounding the central screw hole, wherein the centers of the locking screw holes define a polygon and wherein the center of the central screw hole is located on or within the polygon.

The polygon defined by the locking screw holes may be a triangle, quadrangle (e.g., a tetragon), pentagon, hexagon or any other polygon. In cases in which more than three locking screw holes surround the central screw hole, there may exist at least three locking screw holes defining a triangle such that the center of the central screw hole is located on or within the triangle. The locking screw holes may be immediately adjacent to the central screw hole (i.e., there may be no further hole between the central hole and each locking hole). No internal angle of the polygon may exceed approximately 180°.

Each locking screw hole may include (e.g., a hole portion with) a locking structure adapted to lock a bone fastener to the implant. The locking structure can include a threaded portion or a circumferential lip adapted to lockingly engage a bone fastener. Alternatively, the locking structure may have one or more protrusions extending in a radial direction of the locking screw hole. A bone fastener can be polyaxially or monoaxially insertable through the locking screw hole, such that the locking structure may receive a head portion of a bone fastener for locking engagement therebetween. Alternatively, a bone fastener having a self-cutting portion can be inserted into the locking screw hole for engaging the locking structure. The locking structure of each locking screw hole can be realized in the form of any of the hole configurations described in DE 43 43 117 or U.S. Pat. No. 6,322,562.

The shaft region of the implant may be shaped to conform to an extra-articular part of a bone and the head region of the implant may be shaped to conform to a periarticular part of the bone. The head region may generally be round (e.g., oval or circular). As an example, the implant may generally have a spoon-like shape (with a generally round or oval head) or a L-like shape (with a generally linear head).

A transition from the shaft region to the head region may be defined by an increasing width in an axial direction of the implant. Further, a (e.g., maximal) width of a portion of the head region facing the shaft region may be greater than a (e.g., maximal) width of the shaft region. Thus, the head region may start when a width of the implant continuously enlarges in the distal direction of the implant.

The head region can have a length approximately between 10 mm and 100 mm and a width approximately between 10 mm and 50 mm. Alternatively, the head region may have a width varying over the entire length thereof. Moreover, the width of the head region may be greater than a width of the shaft region. The head region may have an I-, T-, L-, cloverleaf- or calcaneal-shape.

The central screw hole can have a first diameter and each of the locking screw holes can have a second diameter, wherein the first diameter is greater than the second diameter. The diameter of the central screw hole can approximately be between 1 mm and 10 mm, in particular between 6 mm and 9 mm. The diameter of each locking screw hole can approximately be between 1 mm and 10 mm, in particular between 6 mm and 9 mm.

Further, the central screw hole may be located in a central portion of the head region, wherein the locking screw holes surround the central screw hole such that a distance between a center of the central screw hole and a center of each of the locking screw holes does not exceed twice or three times the diameter of the central screw hole.

The central screw hole may be located in a central portion of the head region such that a shortest distance between the center of the central screw hole and a polygon line defined by two neighbouring locking screw holes is approximately between mm and 15 mm, preferably between 3 mm and 12 mm, and in particular approximately between 4 mm and 9 mm.

An angular distance between each pair of neighboring locking screw holes relative to an axis through the center of the central screw hole may not exceed 180°, preferably 170°. Further, the angular distance may not exceed 120°.

The central screw hole may comprise a cylindrical hole portion on a bone contacting side of the implant and/or a curved (e.g., a spherical) or conical hole portion on a side opposite to the bone contacting side. In one implementation, the central screw hole allows to insert a central screw at a selected angle relative to an implant surface.

At least one of the locking screw holes may have a multiple thread (e.g., a double thread). Further, at least one of the locking screw holes may comprise a threaded hole portion on a bone contacting side of the implant and an unthreaded hole portion on a side opposite to the bone contacting side. The threaded hole portion can taper inwardly toward a bone contacting surface of the implant (e.g., in a conical fashion). The unthreaded hole portion can have an inward taper having a curved or conical shape, for example, a spherical shape. The threaded hole portion may have a depth extending toward the bone contacting side of the implant. The depth of the threaded hole portion can approximately be between 0.5 mm and 5 mm, preferably between 0.5 mm and 3 mm. The unthreaded hole portion may have a depth extending from an upper side of the implant toward the bone contacting side and the threaded hole portion respectively. The depth of the unthreaded hole portion can approximately be between 0.5 mm and 5 mm, preferably between 0.5 mm and 3 mm. Further, the depth of the threaded hole portion may be greater than the depth of the unthreaded hole portion the closer the at least one of the locking screw holes is to a distal end or a peripheral side of the head portion.

The shaft portion of the implant may further include at least an oblong hole (e.g., at an end facing the head). Moreover, the oblong hole may include a cylindrical hole portion on a bone contacting side of the implant and a curved or conical hole portion on a side opposite to the bone contacting side. The oblong hole can have a length approximately between 5 mm and 10 mm and a width approximately between 2 mm and 8 mm. The oblong hole may have a region of tapering width between a region of maximum width and a region of minimum width. The oblong hole may also be at least partially threaded.

The head region may include at least one K-wire (Kirschner wire) hole for receiving a K-wire, wherein a diameter of the K-wire hole is smaller than a diameter of each of the central screw hole and the surrounding screw holes. The diameter of the K-wire hole may be approximately between 1 mm and 3 mm. The K-wire hole can further include a threaded hole portion. In one implementation, the head region may include at least one targeting structure (comprising, e.g., a targeting hole) for receiving a targeting instrument. The targeting structure may include grooves on an implant surface. The grooves can substantially extend in the radial direction of a targeting hole.

At least one hole of the implant may have a central axis which is oblique relative a vertical axis of the implant. An angle defined between the central axis and the vertical axis can be approximately between 0° and 60°. Alternatively, the at least one hole may be oblique relative to an upper surface or lower surface of the implant.

An outer peripheral surface of the shaft region may have an undulating shape, such that the shaft region can have a waisted shape. Further, the shaft region may have a length approximately between 40 mm and 400 mm and a width approximately between 5 mm and 20 mm. Alternatively, the width can vary over the entire length of the shaft region. The shaft region can further have a curved shape (e.g., C-shape) in a longitudinal direction thereof.

The locking screw holes may be adapted to receive cortical screws for fixing the implant to bone. The implant can be configured as a bone plate. The implant may have a length approximately between 50 mm and 500 mm and a width approximately between 5 mm and 50 mm. Alternatively, the width can vary over the entire length of the implant. Moreover, the implant can have a thickness approximately between 1 mm and 6 mm. Alternatively, the thickness can vary over the entire length of the implant.

According to a further aspect, there is provided an implant system comprising an implant with a shaft region having one or more holes for receiving bone fasteners, and a head region extending from the shaft region and having a plurality of circular holes for receiving bone fasteners. The plurality of circular holes includes a central (threaded or unthreaded) screw hole having a center and at least three locking screw holes each having a center and surrounding the central screw hole, wherein the centers of the locking screw holes define a polygon and wherein the center of the central screw hole is located on or within the polygon. The implant system further comprises a compression screw adapted to be inserted into the central screw hole, and at least three locking screws or cortical screws adapted for locking engagement with the locking screw holes.

Each locking screw hole of the implant may include a hole portion with a locking structure adapted to lock a bone fastener to the implant. The locking structure may be configured as generally described above.

The implant may further comprise an oblong hole for receiving a further compression or locking screw.

The head region of the implant may include at least one targeting structure for receiving a targeting instrument. The targeting structure can include a targeting hole.

According to a further aspect, there is provided a system comprising an implant with a shaft region having one or more holes for receiving bone fasteners, and a head region extending from the shaft region and having a plurality of circular holes for receiving bone fasteners. The plurality of circular holes includes a central (threaded or unthreaded) screw hole having a center and at least three (threaded or unthreaded) locking screw holes each having a center and surrounding the central screw hole, wherein the centers of the locking screw holes define a polygon and wherein the center of the central screw hole is located on or within the polygon.

The system may further comprise a targeting instrument adapted to be secured to the implant.

The head region of the implant may further include at least one targeting structure comprising, e.g., a targeting hole for receiving the targeting instrument. A portion of the targeting instrument can be adapted to be fixedly secured to the targeting structure of the implant. Further, the targeting instrument may include a plurality of guide holes for guiding bone fasteners, drilling instruments or guiding instruments.

According to a further aspect, there is provide a method for fracture fixation of bone comprising the steps of fixing an implant against bone with at least one bone fastener, wherein the implant comprises a shaft region having one or more holes for receiving bone fasteners, and a head region extending from the shaft region and having a plurality of circular holes for receiving bone fasteners, the plurality of circular holes including a central (threaded or unthreaded) screw hole having a center and at least three locking screw holes each having a center and surrounding the central screw hole, wherein the centers of the locking screw holes define a polygon and wherein the center of the central screw hole is located on or within the polygon; inserting a compression screw through the central screw hole of the implant into bone for compressing the fracture of bone; and inserting at least three locking screws or cortical screws into the locking screw holes of the implant for producing a locking engagement therebetween, thereby stabilizing the truss formed by the implant, the screws and bone.

A method for fracture fixation using the system described herein may comprise fixing an implant against bone with at least one bone fastener. The implant comprises a shaft region having one or more holes for receiving bone fasteners. The implant has a head region extending from the shaft region and having a plurality of circular holes for receiving bone fasteners, the plurality of circular holes including a central screw hole having a center and at least three locking screw holes each having a center and surrounding the central screw hole. The centers of the locking screw holes define a polygon and the center of the central screw hole is located on or within the polygon. A compression screw is inserted through the central screw hole of the implant into bone for compressing the fracture of bone. At least three locking screws or cortical screws are inserted into the locking screw holes of the implant for producing a locking engagement therebetween, thereby stabilizing the truss formed by the implant, the screws and bone.

Due to the fact that the center of the central screw hole is located on or within a polygon defined by the centers of the locking screw holes, the head portion has a defined hole configuration which guarantees a desired high screw-plate-bone construct stability. Therefore, the implant provides an optimal biomechanical stability and better resistance to pull out. Further, the implant cannot lose the contact to bone and cannot be shifted in an undesired direction. Thus, the medical success increases and rapid healing is achieved.

BRIEF DESCRIPTION OF THE DRAWINGS

These and other features, aspects and advantageous of the present disclosure will become apparent from the following detailed description taken in conjunction with the accompanying drawings, wherein.

DETAILED DESCRIPTION

Figure 1:
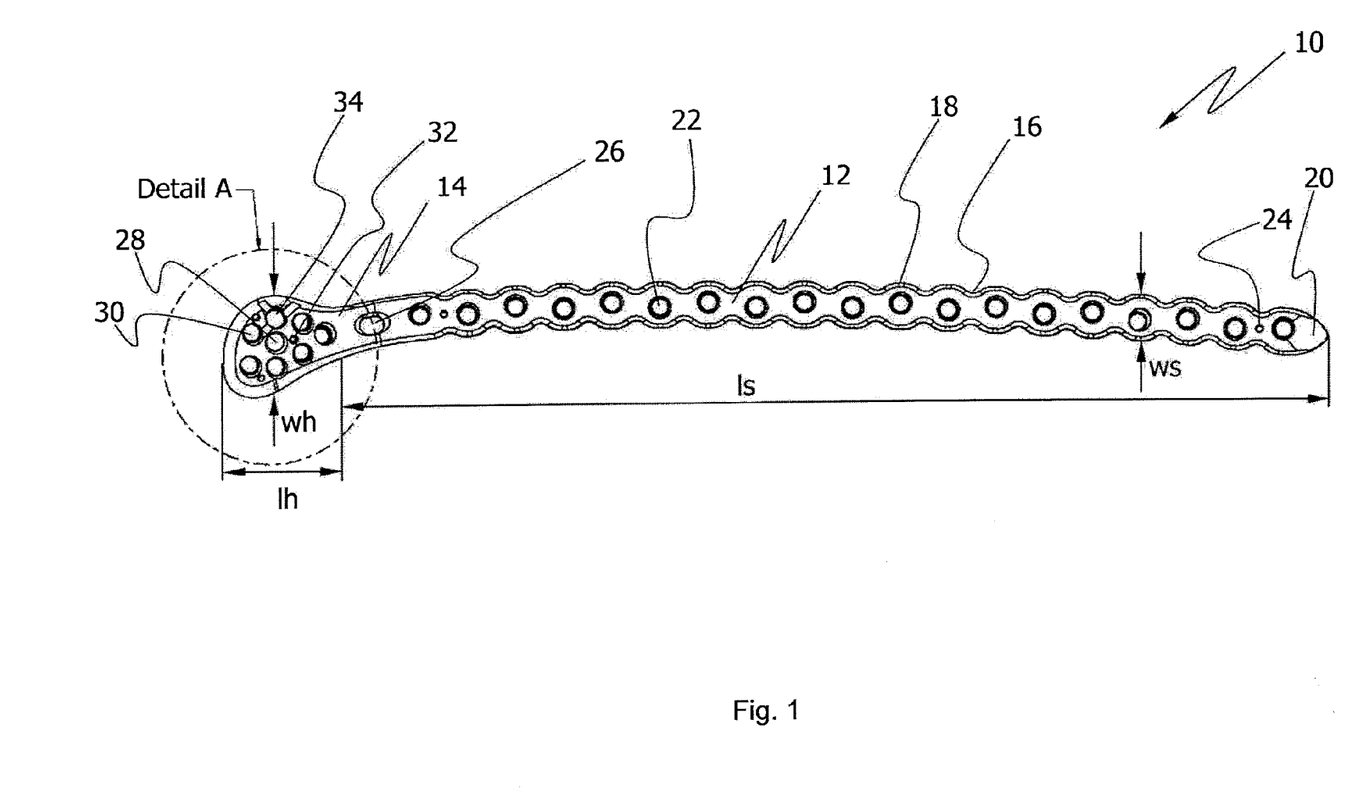
FIG. 1 is a top view of an implant embodiment.

Referring to FIG. 1, there is shown a top view of a first embodiment of an implant in form of a bone plate 10 for use in orthopedic surgery for fixation of bone (not shown in FIG. 1). The bone plate 10 has a length of approximately 380 mm and a width of approximately 40 mm. As shown in FIG. 1, the width of bone plate 10 varies over the entire length of the bone plate 10. Further, the bone plate 10 has a maximum thickness of approximately 5 mm. Also the thickness of the bone plate can vary over the entire length of bone plate 10. For facilitating the arrangement of bone plate 10 within a patient's body, the bone plate 10 includes a portion along the outer peripheral side thereof which may be angled.

The bone plate 10 is made of a biocompatible material such as stainless steel, titanium or a titanium alloy, and comprises a shaft region 12 and a head region 14 extending from the shaft region 12. The shaft region 12 is shaped to conform to an extra-articular part of a bone such as the diaphyseal part of bone. Further, the shaft region 12 has a length is of approximately 330 mm and a maximum width ws of approximately 16 mm. As illustrated in FIG. 1, the shaft region 12 has an undulating or waisted shape. Thus, the width of the shaft region varies over the entire length thereof, wherein the shaft region 12 includes a plurality of valleys 16 and a plurality of peaks 18. The waisted plate shape of the shaft region 12 provides a uniform load transfer. Further, the shaft region 12 has a curved shape (e.g., C-shape) in a longitudinal direction thereof to adapt to the form of a bone.

As shown in FIG. 1, the shaft region 12 has a rounded and tapered plate end 20 for facilitating sliding of plate 10 submuscularly. The shaft region 12 further includes a plurality of holes for receiving bone fasteners such as locking screws, non-locking screws and bone pegs (not shown in FIG. 1). Circular screw holes 22 for receiving locking screws or cortical screws are arranged on the shaft region 12 along the longitudinal direction of the shaft region 12 in an undulating form. Thereby, each circular screw hole 22 is located between two peaks 18 facing each other. The shaft region 12 of the bone plate 10 further includes K-wire (Kirschner-wire) holes 24 for receiving a K-wire. These K-wire holes 24 are used for primary and temporary fixing the bone plate 10 to the fractured bone. A diameter of the K-wire hole 24 is smaller than a diameter of each of the circular screw holes 22, wherein the diameter of the K-wire hole 24 is approximately 2.5 mm.

As also illustrated in FIG. 1, the shaft region 12 of bone plate 10 includes an oblong hole 26 at end facing the head region 14. The oblong hole 26 has a length of approximately 10 mm and a maximum width of approximately 7 mm. Bone fasteners can be polyaxial inserted in the oblong (e.g., elongated) hole 26 (not shown in FIG. 1)

As further shown in FIG. 1, the head region 14 of bone plate 10 is generally rounded such as an oval or circle. Thus, the bone plate 10 generally has a spoon-shape. Further, the head region 14 is shaped to conform to a periarticular part of the bone such as the metaphyseal or epiphyseal part of bone, and includes a plurality of circular holes for receiving bone fasteners. The head region has a length lh of approximately 50 mm and a maximum width wh of approximately 40 mm. As also illustrated in FIG. 1, the width of the head region 14 varies over the entire length of the head region 14, and the width wh of the head region 14 is greater than the width ws of the shaft region 12.

An unthreaded central screw hole 28 is located in a central portion of the head region 14, and locking screw holes 30 such as threaded screw holes 30 surround the central screw hole 28. The central screw hole 28 can receive compression or cortical screws for providing compression of a fracture by pushing bone fragments towards each other. The surrounding screw holes 30 can selectively receive locking screws or cortical screws for fixing the bone plate 10 to bone. Once locking screws (not shown in FIG. 1) are inserted in the surrounding screw holes 30, a monoaxial engagement therebetween is provided for allowing axially stable screw placement to bring stability to the construct formed by the screws, plate and bone. Further, each surrounding screw hole 30 includes a locking structure. The locking structure of each surrounding screw hole 30 is a threaded portion which may be a multiple thread in the form of, e.g., a double thread (i.e., a double-lead thread). Also the head region 14 includes K-wire holes 32 for receiving a K-wire to primary and temporary fix the bone plate 10 to bone as described above with regard to the shaft region 12. For receiving a targeting instrument (not shown in FIG. 1), the head region 14 includes a targeting structure 34 in the form of a targeting hole.

Figure 2:
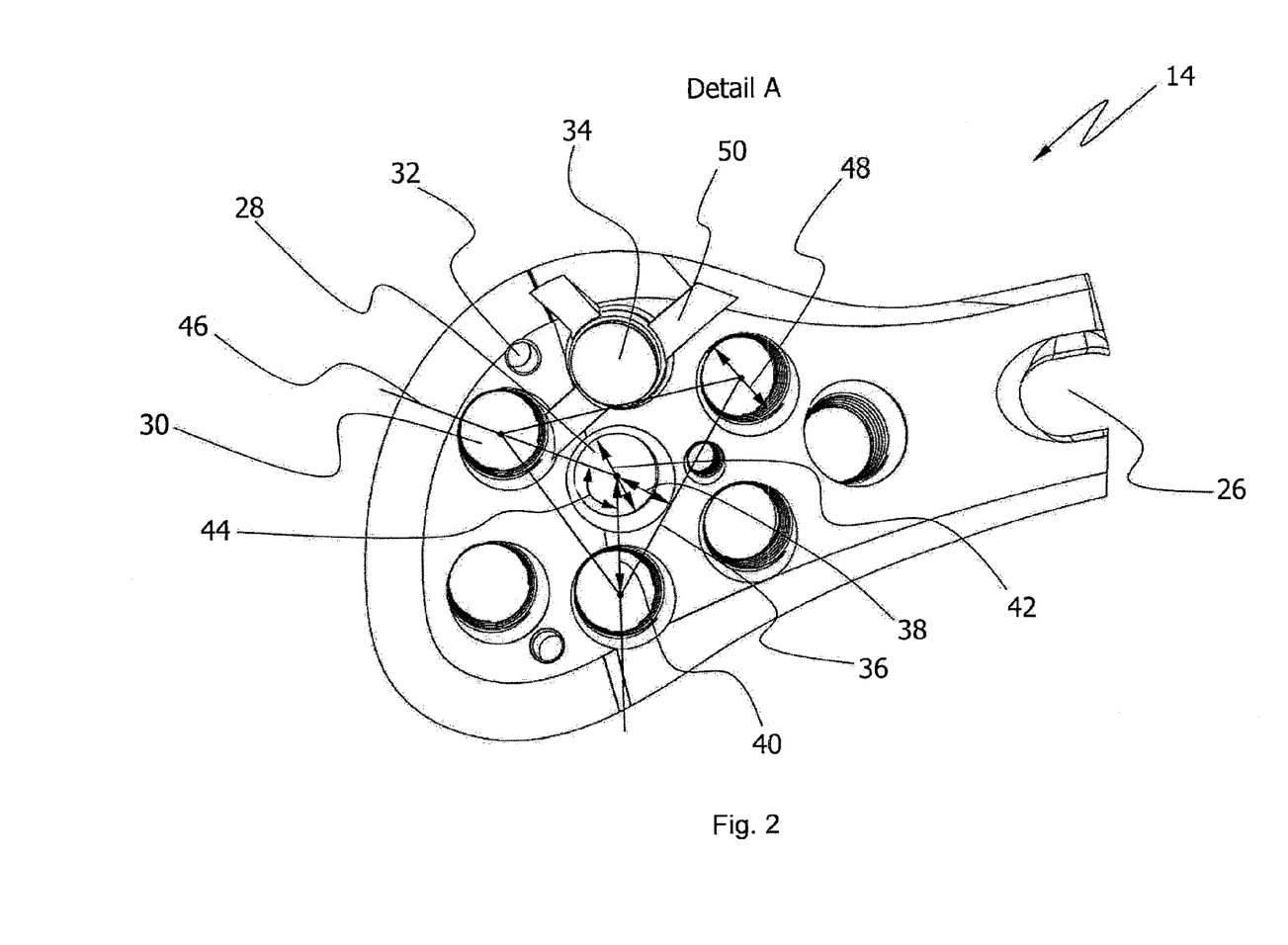
FIG. 2 is a detailed view of the head portion of the implant shown in FIG. 1.
Figure 2A:
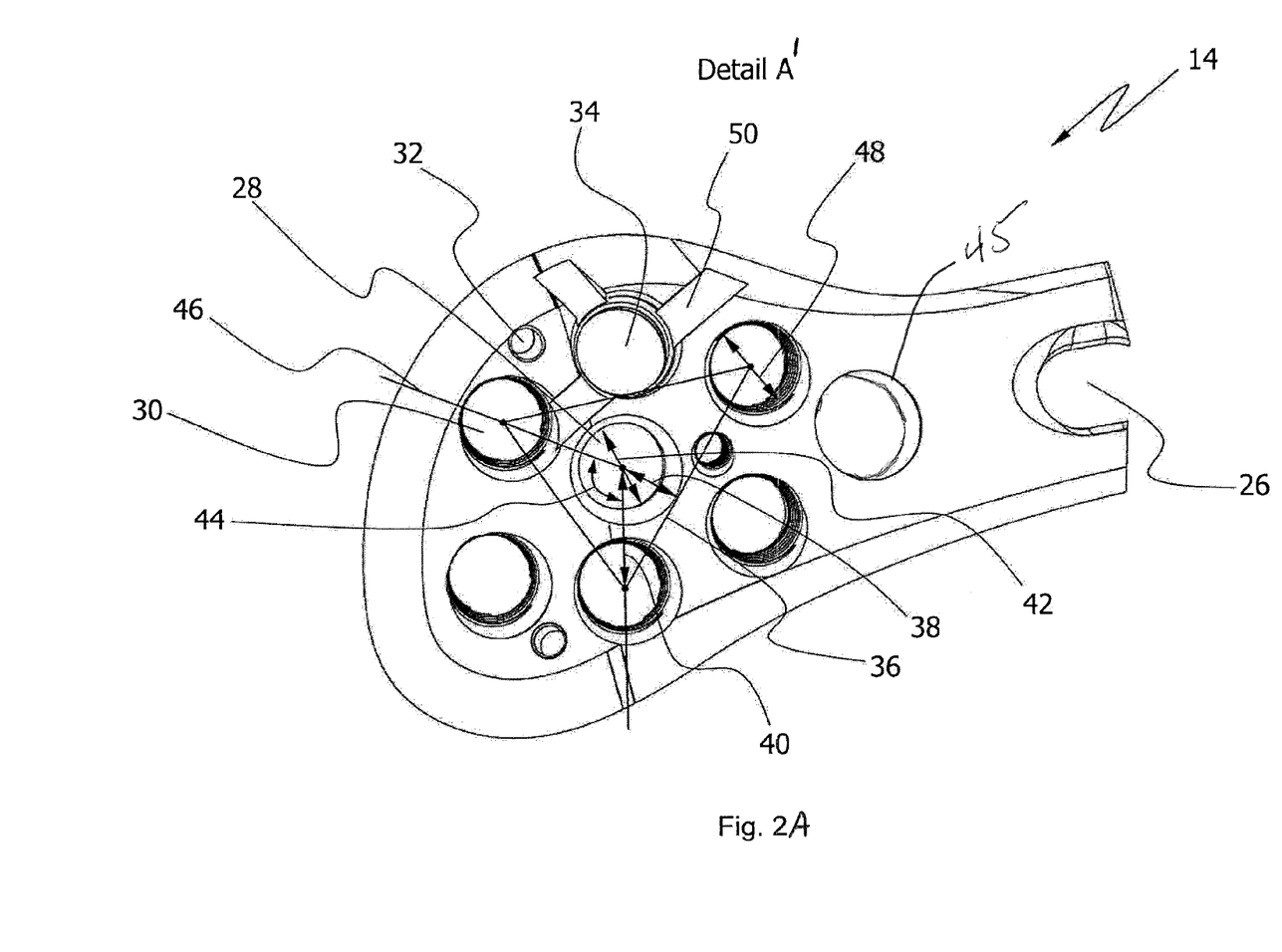
FIG. 2A is a detailed view of the head portion of FIG. 1 with a second unthreaded hole in the head portion.

FIG. 2 illustrates in a schematic form a detailed view of the head region 14 of bone plate 10 shown in FIG. 1 (Detail A) to illustrate certain geometrical features of the circular screw hole configuration. As shown in FIG. 2, the central screw hole 28 and each of the threaded surrounding screw holes 30 has a center. The centers of the surrounding screw holes 30 define a polygon 36 in the form of, e.g., a triangle. The polygon may be defined by the centers of three, four or five surrounding screw holes 30 closest to the central screw hole 28. Optionally, the polygon can be defined by the centers of several surrounding screw holes 30 adjacent to the central screw hole 28. It should be noted that not all the surrounding screw holes 30 need to constitute the polygon. Further, as shown in FIG. 2, the center of the central screw hole 28 is located within the polygon 36. Alternatively, the center of the central screw hole 28 may be located on the polygon 36 (i.e., on a line connecting the centers of two of the surrounding screw holes 30 that define the polygon). As illustrated in FIG. 2, the surrounding screw holes 30 are immediately adjacent to the central screw hole 28, such that there is no further hole between the central screw hole 28 and each surrounding screw hole 30. FIG. 2A shows a second alternate view of the head region (detail A) with a second unthreaded head hole 45.

As also illustrated in FIG. 2, the center of the central screw hole 28 has a distance 38 from a polygon line defined by the centers of two neighboring surrounding screw holes 30. This distance 38 is preferably the shortest distance which is approximately between 1 mm and 15 mm, and is approximately 6 mm in the embodiment of FIG. 2.

The central screw hole 28 is located in a central portion of the head region 14, wherein the surrounding screw holes 30 surround the central screw hole 28 such that a distance 40 between the center of the central screw hole 28 and the center of each of the surrounding screw holes 30 does not exceed twice a diameter 42 of the central screw hole 28. Moreover, an angular distance 44 between each pair of neighboring surrounding screw holes 30 relative to an axis 46 through the center of the central screw hole 28 does not exceed 180°, preferably 170°, and is approximately 120° in the embodiment of FIG. 2.

As shown in FIG. 2, each of the surrounding screw holes has a diameter 48, wherein the diameter 42 of the central screw hole 28 is greater than the diameter 48 of each surrounding screw hole 30. Therefore, the central screw hole 28 can receive large compression or cortical screws having a greater shaft diameter. The diameter 42 of the central screw hole 28 is approximately 6 mm. The diameter 48 of each surrounding screw hole 30 is approximately slightly smaller than 6 mm.

The K-wire holes 32 of the head region 14 have a diameter which is smaller than the diameter of each of the central screw hole 28 and the surrounding screw holes 30. The diameter of each K-wire hole 32 is approximately 2.5 mm. The targeting structure 34 is located near a peripheral side of the head region 14, and is in the form of a targeting hole having a threaded hole portion for receiving a targeting instrument. The targeting hole 34 has grooves 50 extending substantially in the radial direction of the targeting hole 34 for stabilizing the targeting instrument.

Figure 3:
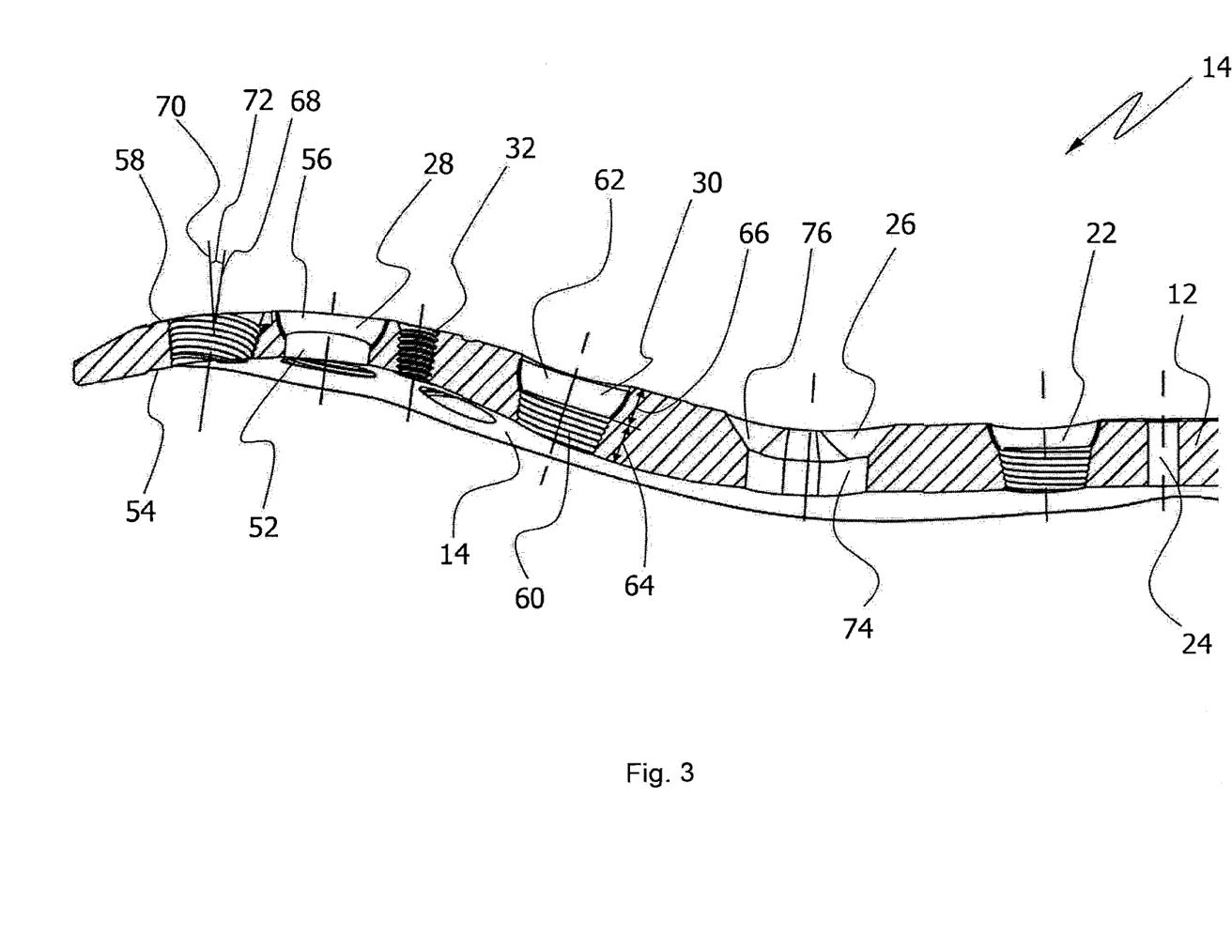
FIG. 3 is a cross-sectional view of the head portion shown in FIG. 2.

FIG. 3 illustrates a cross-sectional view of the head region 14 shown in FIG. 2. The central screw hole 28 comprises a cylindrical hole portion 52 on a bone contacting side 54 of the bone plate 10 and a curved, e.g., spherical hole portion 56 on a side 58 opposite to the bone contacting side 54. The central screw hole 28 can polyaxially (i.e., at an angle selected by the surgeon) receive compression or cortical screws, wherein a screw head seats on the spherical hole portion 56 (not shown in FIG. 3).

As shown in FIG. 3, the surrounding screw holes 30 include a threaded hole portion 60 on the bone contacting side 54 of the bone plate 10 and an unthreaded hole portion 62 on the side 58 opposite to the bone contacting side 54. Thus, the surrounding screw holes 30 may receive a locking screw, wherein a threaded head of the locking screw mates with the threaded hole portion 60 for providing an angular stable locking engagement therebetween at a predefined angle (i.e., monoaxially). Optionally, the surrounding screw holes 30 can receive cortical screws, wherein the screw head seats on the unthreaded hole portion. The unthreaded hole portion 62 has an inward taper having a curved shape (e.g., a spherical surface). Further, the threaded hole portion 60 tapers inwardly toward the bone contacting surface 54 in a conical fashion.

A depth 64 of the threaded hole portion 60 extending toward the bone contacting side 54 of bone plate 10 is approximately between 0.5 mm and 5 mm, and is approximately 3 mm in the embodiment of FIG. 3. The unthreaded hole portion 62 has a depth 66 extending from the upper side 58 of the bone plate 10 toward the threaded hole portion 60 and the bone-contacting side respectively. The depth 66 of the unthreaded hole portion 62 is approximately between 0.5 mm and 5 mm, and is approximately 2 mm in the embodiment of FIG. 3. Moreover, as shown in FIG. 3, the depth 64 of the threaded hole portion 60 is greater than the depth 66 of the unthreaded hole portion 62 the closer the surrounding screw hole 30 is to a distal end or a peripheral side of the head region 14.

As illustrated in FIG. 3, the circular screw holes 22 of shaft region 12 may have the hole design of the surrounding screw holes 30 of the head region 14 as described above.

It can be seen from FIG. 3 that each hole of the bone plate 10 can have a different angular orientation with respect to the bone plate 10. This angular orientation is defined by a central axis 68 of the hole and a vertical axis 70 of the bone plate 10. Therefore, as shown in FIG. 3, the central axis 68 of the circular holes can be oblique relative to the vertical axis 70 of the bone plate 10, wherein an angle 72 is defined between the central axis 68 and the vertical axis 70. This angle 70 can be approximately between 0° and 60°. Moreover, the circular holes can be oblique relative to the upper surface 58 or the lower surface 54 of the bone plate 10.

As shown in FIG. 3, the oblong or elongated hole 26 includes a cylindrical hole portion 74 on the bone contacting side 54 and a tapered, conical hole portion 76 on the side 58 opposite to the bone contacting side 54. After a bone fastener is monoaxial or polyaxial inserted through the oblong hole 26, the head of the bone fastener (e.g., screw head) seats on the conical hole portion 76 (not shown in FIG. 3). As further illustrated in FIG. 3, the K-wire holes can include a threaded hole portion 78.

Figure 4:
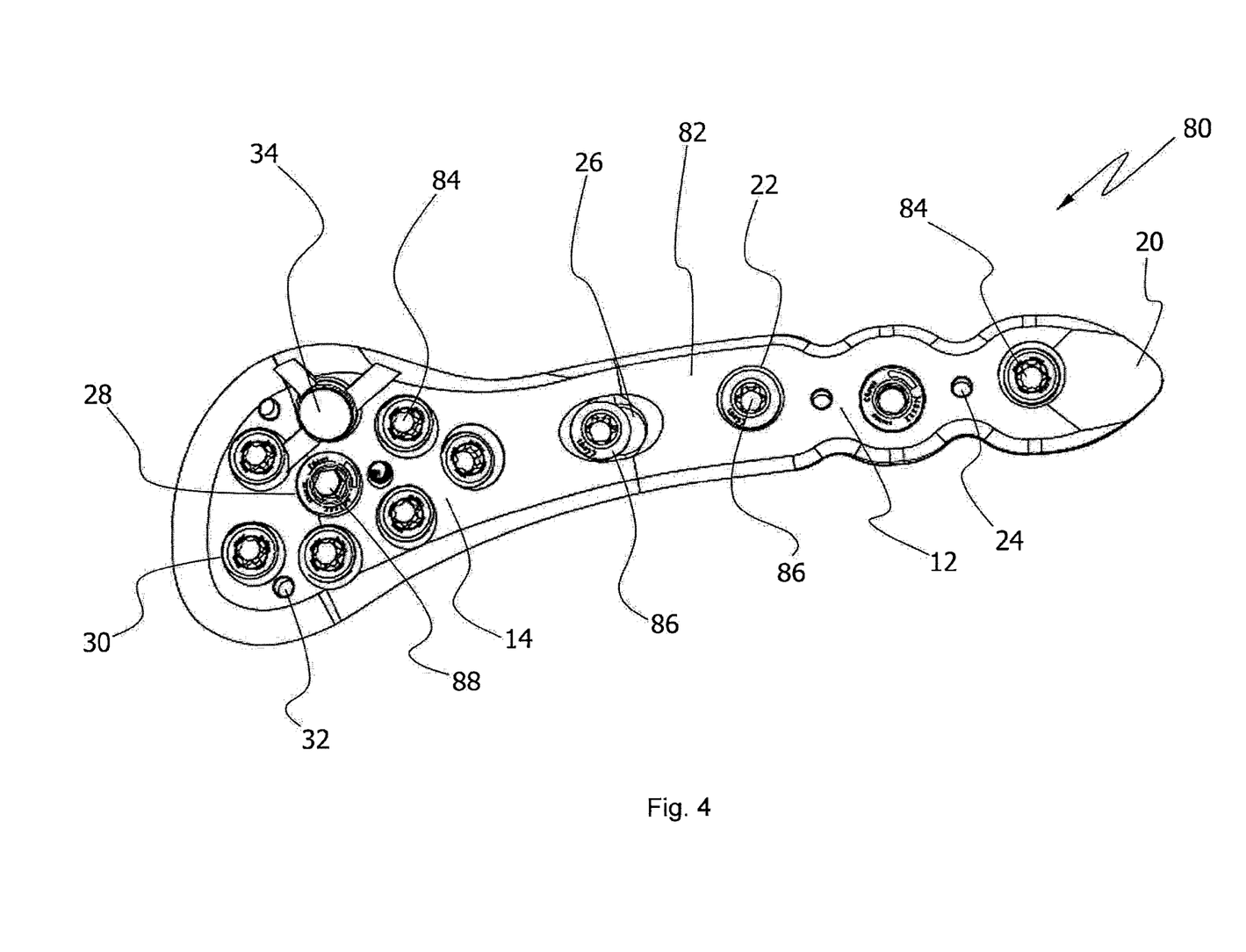
FIG. 4 is a top view of a dummy implant system embodiment.
Figure 5:
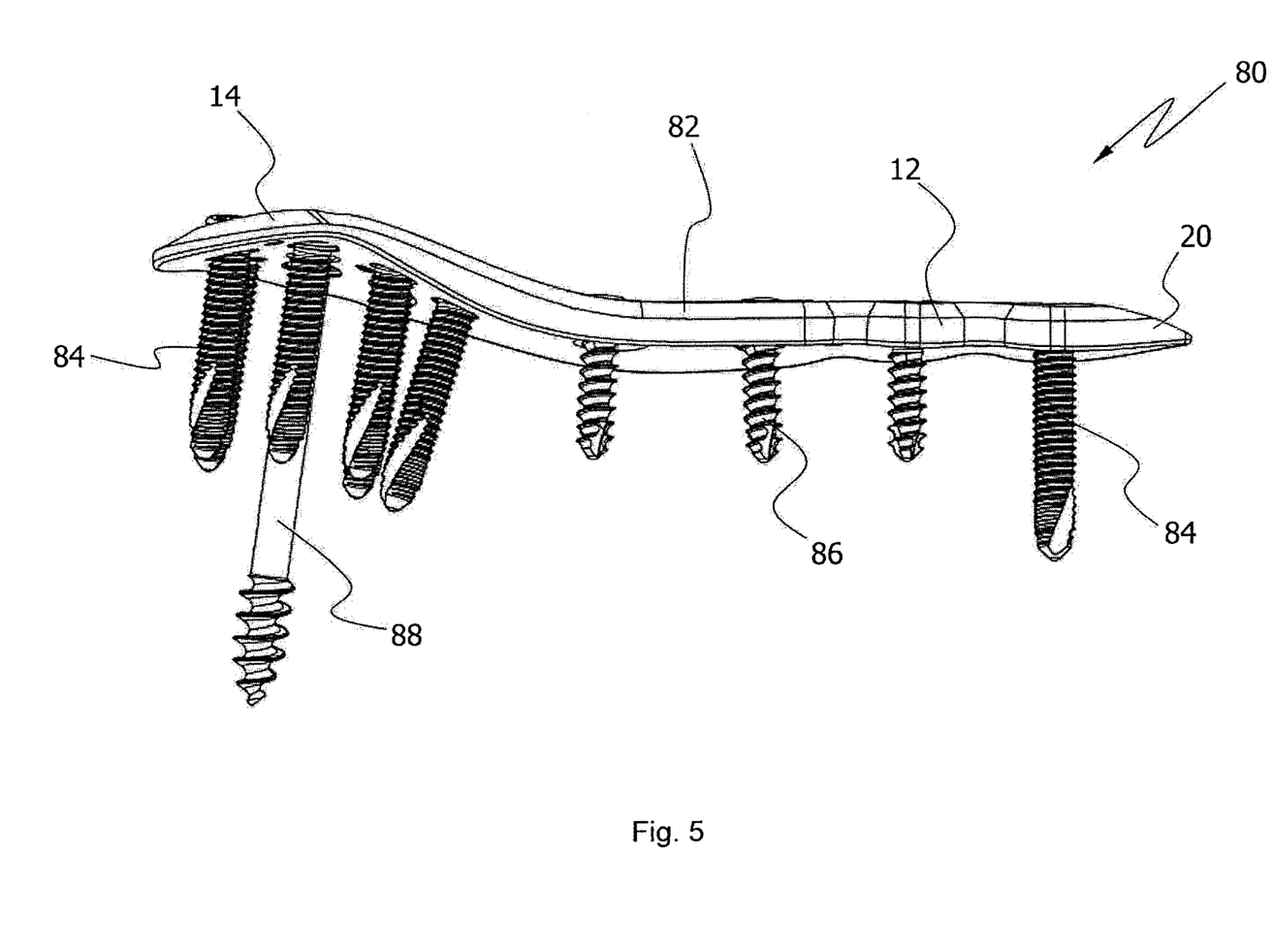
FIG. 5 is a side view of the dummy implant system shown in FIG. 4.
Figure 6:
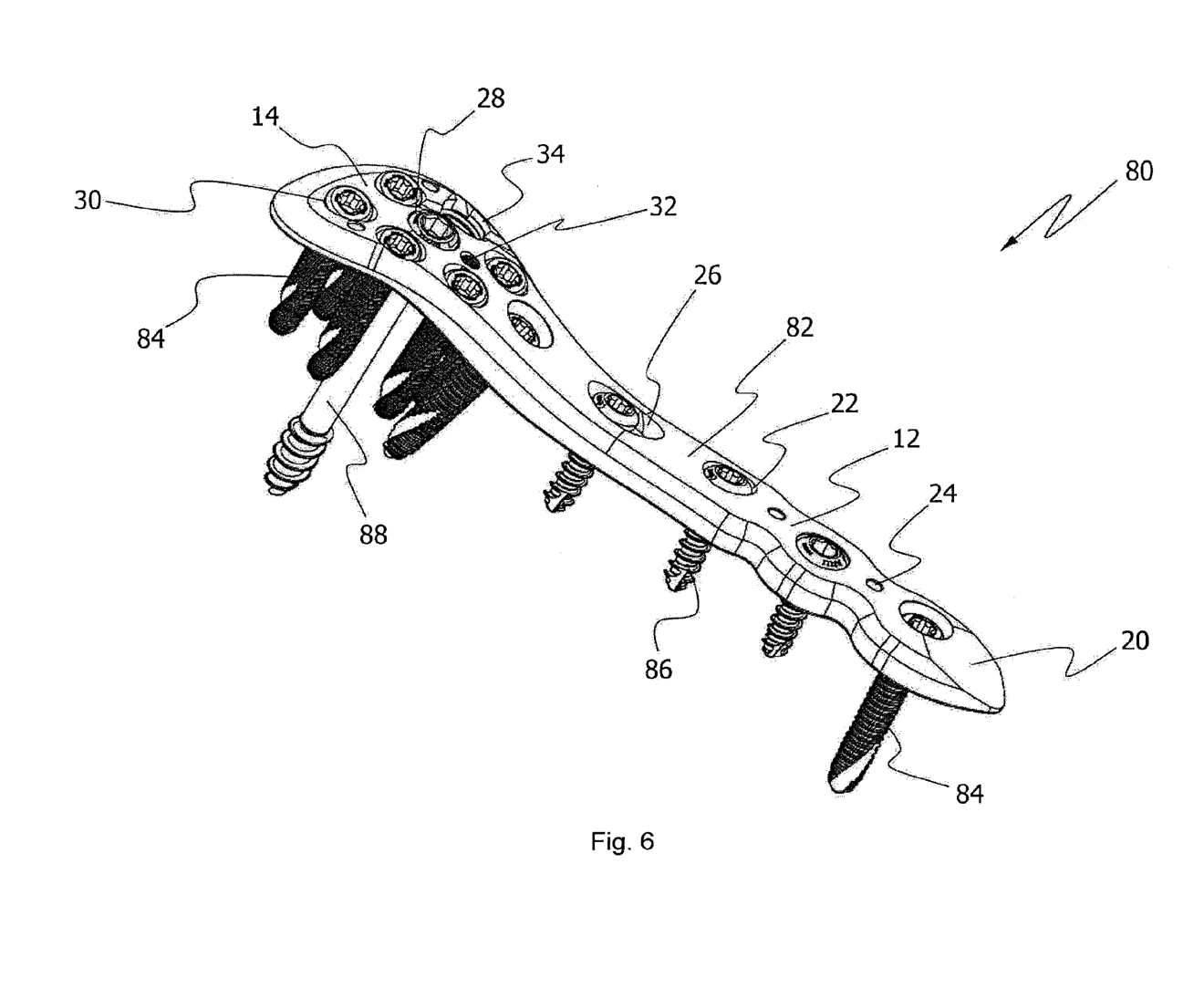
FIG. 6 is a perspective view of the dummy implant system shown in FIGS. 4 and 5.

FIGS. 4 to 6 show an embodiment of an implant system 80 having a dummy bone plate 82 that can be adapted as needed (e.g., in terms of shape, length, width, thickness, etc.) for use in orthopedic surgery for fixation of bone.

FIG. 4 illustrates a top view of the dummy implant system 80 having the bone plate 82, locking screws 84 and compression screws 88. The bone plate 82 has the head and shaft region and its configuration of bone plate 10 shown in FIGS. 1 to 3, wherein the head region includes the defined screw hole configuration as shown in FIG. 2.

FIG. 5 illustrates a side view and FIG. 6 illustrates a perspective view of the dummy implant system 80. As shown in FIGS. 5 and 6, cortical screws 86 are inserted through the circular screw holes 22 of shaft region 12 for fixing the bone plate in a middle portion to bone. Further, another cortical screw 86 is inserted in the oblong hole 26. A locking screw 84 is inserted in the last circular screw hole 22 near the plate end 20 for fixing the bone plate end to bone. Further locking screws 84 are in locking engagement with the surrounding screw holes 30 of the head region 14. The threaded head of the locking screws 84 mates with the internal threaded hole portion 60 of the surrounding screw holes 30 for providing an axially stable engagement. A compression screw 88 in the form of a cancellous screw is inserted through the central screw hole 28, wherein the screw head of the compression screw 88 seats on the spherical hole portion 56 and the shaft of the compression screw 88 is directed in a direction beneath the bone contacting side 54 of bone plate 82. Thus, the compression screw 88 can provide compression of a fracture in a periarticular region of bone by pushing bone fragments towards each other.

As shown in FIGS. 5 and 6, the head region 14 forms in combination with several locking screws 84 inserted through the surrounding screw holes 30 and the compression screw 88 inserted through the central screw hole 28 a stable truss for guaranteeing a desired screw-plate-bone construct stability. Due to the fact that the surrounding screw holes 30 surround the central screw hole 28 with the defined hole configuration as shown in FIG. 2, a pull-out of compression screw 88 is avoided and the bone plate 82 cannot lose the contact to bone.

Figure 7:
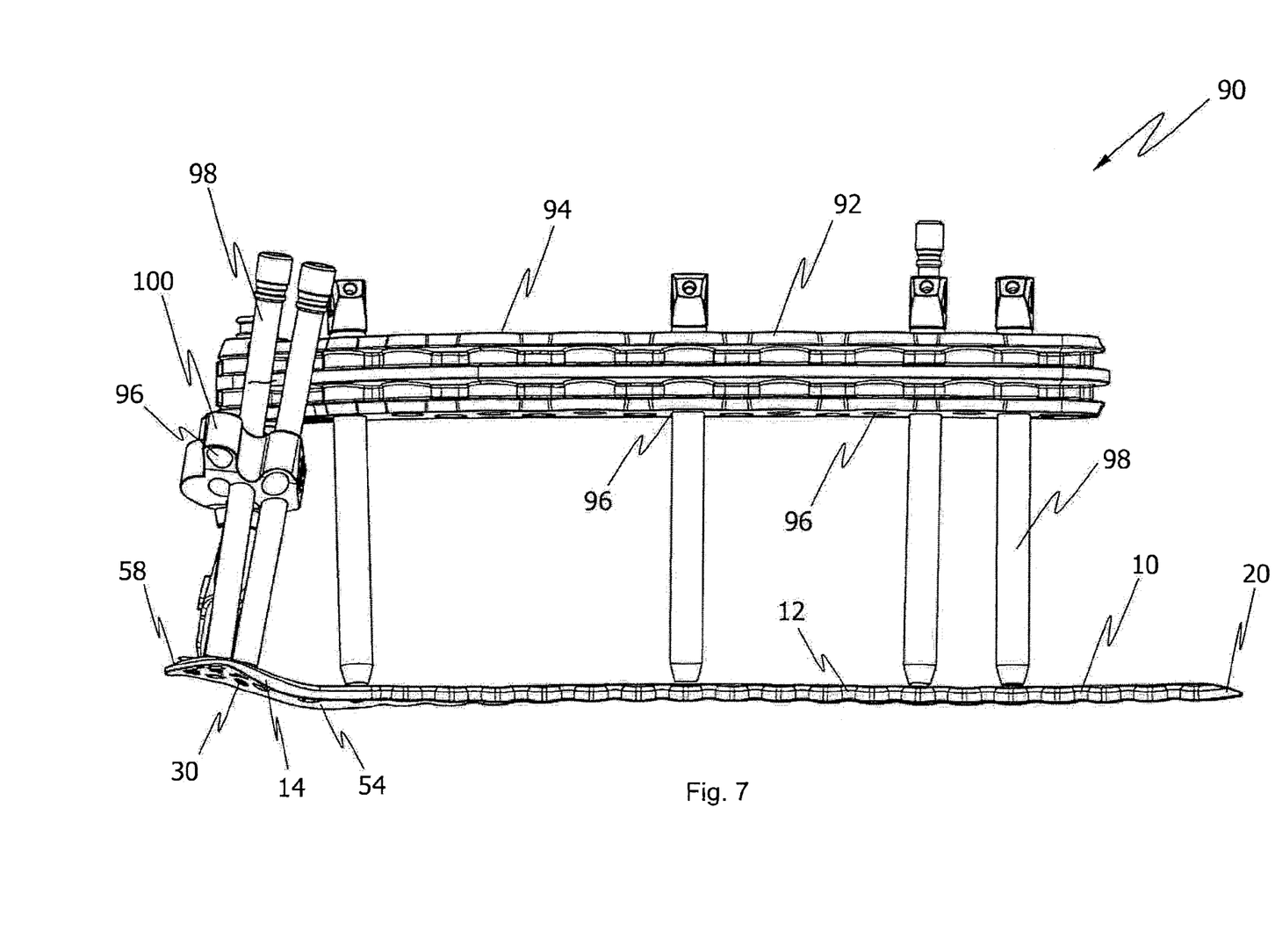
FIG. 7 is a side view of a system including the implant shown in FIGS. 1 to 3 and a targeting instrument.

Referring to FIG. 7, there is shown a system 90 including a targeting instrument 92 and a bone plate 10 as shown in FIGS. 1 to 3, wherein the head region 14 has the defined screw hole configuration as described above with regard to FIG. 2. The targeting instrument 92 includes a body 94 having a plurality of guide holes 96 defined therein. Drilling instruments, guiding instruments 98 or bone fasteners such as bone screws along with instruments utilized for the implantation thereof can be advanced through the guide holes 96. As shown in FIG. 7, the targeting instrument 92 is configured such that the guide holes 96 align with the holes of bone plate 10 once the targeting instrument is fixedly secured to the targeting structure 34 of head region 14 of bone plate 10. The body 94 of the targeting instrument 92 further includes a head portion 100 which can be adapted to the orientation of the head region 14 of bone plate 10. Also the head portion 100 of the targeting instrument 92 includes several guiding holes 96 of guaranteeing a defined orientation of the bone fasteners with respect to the bone plate and the fractured bone respectively. Therefore, the bone fasteners cannot hit each other beneath the bone plate 10 within the bone during the inserting process (e.g., screwing in) of the bone fasteners. Thus, a quick attachment of bone plate 10 to bone and a desired truss formed by the precisely inserted bone fasteners is achieved.

Figure 8:
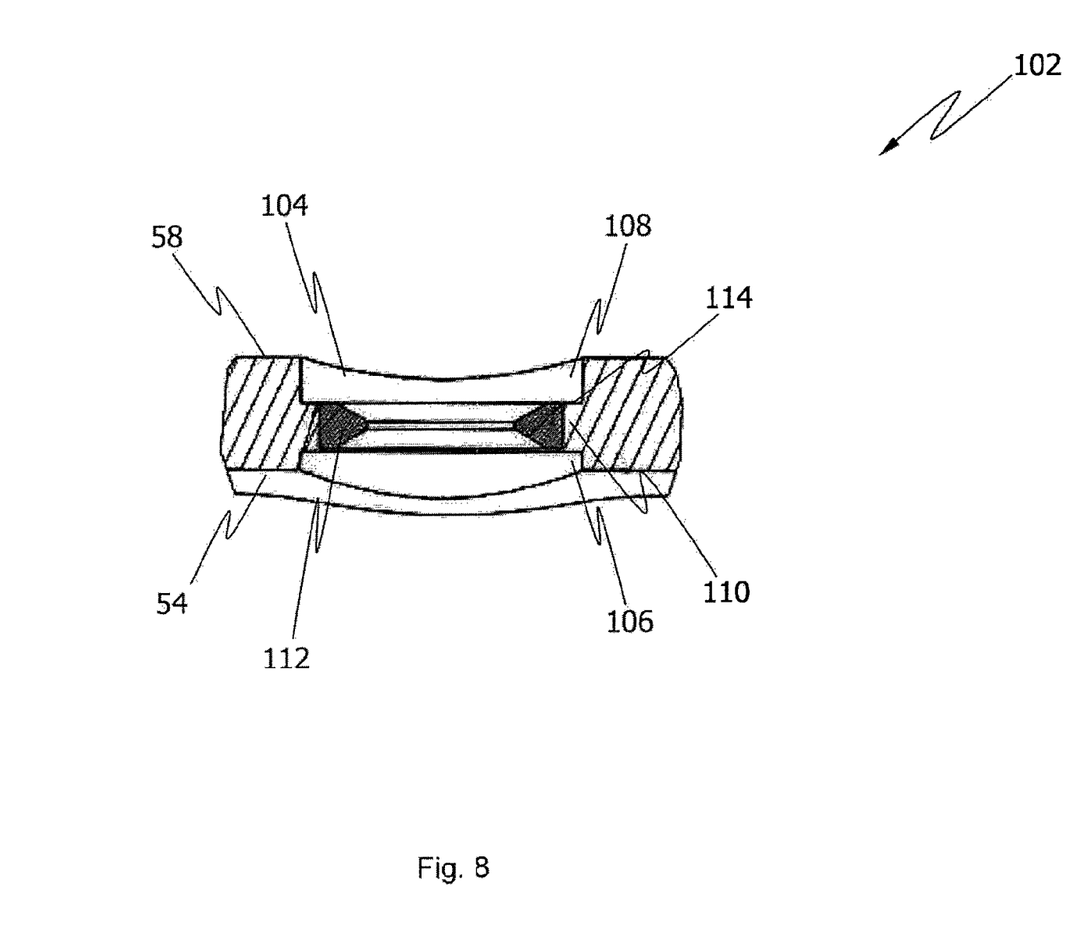
FIG. 8 is a cross-sectional view of an alternative locking screw hole embodiment.

Referring to FIG. 8, there is shown a further embodiment 102 of a locking screw hole 104 for an implant as discussed herein. The locking screw hole 104 includes a lower cylindrical hole portion 106 on the bone contacting side 54 of an implant and an upper cylindrical hole portion 108 on the side 58 opposite to the bone contacting side 54. A middle portion 110 is arranged between the upper and lower cylindrical hole portion. The middle portion 110 includes a circumferential lip 112 having roughly the shape of a triangle. A bone fastener can be polyaxially inserted through the locking screw hole 104, wherein the bone fastener lockingly engages the circumferential lip 112 (see DE 43 43 117 or U.S. Pat. No. 6,322, 562). As further illustrated in FIG. 8, a diameter of the middle portion 110 is smaller than each of a diameter of the upper cylindrical portion 108 and a diameter of the lower cylindrical portion 106. Moreover, the locking screw hole 104 includes a supporting structure 114 defined by the upper cylindrical portion 108. The supporting structure 114 may receive a head portion of a bone fastener (not shown in FIG. 8).

In a method for fracture fixation of bone, the bone plate shown in FIGS. 1 to 3 or 4 to 6 is firstly arranged on a fractured bone (not shown in the Figs.), wherein the shaft region is in contact with an extra-articular region of bone (diaphyseal part) and the head region 14 is in contact with a periarticular region of bone (metaphyseal and/or epiphyseal part). Then, the bone plate is primary and/or temporary fixed against bone with one or more bone fasteners such as K-wires, locking screws 84 or cortical screws 86. A compression screw 88 is then inserted through the central screw hole 28 of the bone plate into bone for compressing the fracture of the bone. Finally, locking screws 84 or cortical screws 86 are inserted through the surrounding screw holes 30 of the head portion 14 of the bone plate into bone for producing a locking engagement therebeteween. Thereby, the truss formed by the bone plate, the inserted screws and bone is stabilized for guaranteeing a desired stability. Therefore, the bone plate cannot be shifted in an undesired direction or cannot be pulled out. Thus, the medical success increases and a rapid healing is achieved.

While the head region 14 of the bone plates 10 and 82 as described above includes a defined screw hole configuration as shown in FIG. 2, the shaft region 12 of the respective bone plate can be adapted to different applications and may thus have different holes and a different shape. Also the shape of the head region 14 may be adapted to different applications. Further, while the bone plate holes shown herein are circular, they could be elongated and be partially threaded.

While the above embodiments has primarily described in relation to bone screws and bone plates, it will be readily apparent that the techniques presented herein can also be implemented in combination with other types of bone fasteners (such as bone pegs having a rod-like or pin-like shafts, wire-like bone fasteners such as Kirschner-wires, etc.) as well as other types of implants (such as bone distractors). Accordingly, the present disclosure is not limited to any type of bone fasteners or any type of implant.

The features described in above taken in conjunction with the accompanying drawings can be readily combined to result in different embodiments. It will thus be apparent that the disclosure described above may be varied in many ways. Such variations are not to be regarded as a departure from the scope of the disclosure, and all such modifications as would be apparent to one skilled in the art are intended to be included within the scope of the following claims.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An implant, comprising
a shaft region having one or more holes for receiving bone fasteners; and
a head region extending from the shaft region and having a plurality of circular holes for receiving bone fasteners, the plurality of circular holes including an unthreaded central screw hole having a center and at least three threaded locking screw holes each having a center and surrounding the central screw hole, wherein the centers of the locking screw holes define a polygon and wherein the center of the central screw hole is located on or within the polygon,
wherein the central screw hole comprises a part-spherical or conical hole portion on a side opposite the bone contacting side of the implant; and
a targeting hole located intermediate two of the threaded locking screw holes, the targeting hole having grooves extending substantially radially therefrom on the side opposite the bone contacting side for stabilizing a targeting instrument.

2. The implant according to claim 1, wherein each locking screw hole includes a locking structure adapted to lock a bone fastener to the implant.

3. The implant according to claim 2, wherein the locking structure includes a threaded portion or a circumferential lip adapted to engage the bone fastener.

4. The implant according to claim 1, wherein the shaft region is shaped to conform to an extra-articular part of a bone and the head region is shaped to conform to a periarticular part of the bone.

5. The implant according to claim 1, wherein the central screw hole has a first diameter and each of the locking screw holes has a second diameter, wherein the first diameter is greater than the second diameter.

6. The implant according to claim 1, wherein the central screw hole is located in a central portion of the head region and wherein the locking screw holes surround the central screw hole such that a distance between the center of the central screw hole and the center of each of the locking screw holes does not exceed three times a diameter of the central screw hole.

7. The implant according to claim 1, wherein the central screw hole is located in a central portion of the head region such that a shortest distance between the center of the central screw hole and a polygon portion defined by two neighbouring locking screw holes is between 1 mm and 15 mm.

8. The implant according to claim 1, wherein an angular distance between each pair of neighboring locking screw holes relative to an axis through the center of the central screw hole does not exceed 170°.

9. The implant according to claim 8, wherein the angular distance does not exceed 120°.

10. The implant according to claim 1, wherein the central screw hole comprises a cylindrical hole portion on a bone contacting side of the implant and a curved or conical hole portion on a side opposite to the bone contacting side.

11. The implant according to claim 1, wherein at least one of the locking screw holes comprises a threaded hole portion on a bone contacting side of the implant and an unthreaded hole portion on a side opposite to the bone contacting side.

12. The implant according to claim 11, wherein the threaded hole portion tapers inwardly toward a bone contacting surface of the implant.

13. The implant according to claim 11, wherein the unthreaded hole portion has an inward taper having a curved or conical shape.

14. The implant according to claim 1, wherein the shaft portion further includes an oblong hole.

15. The implant according to claim 1, wherein the head region further includes at least one K-wire hole for receiving a K-wire, wherein a diameter of the K-wire hole is smaller than a diameter of each of the central screw hole and the locking screw holes.

16. The implant according to claim 1, wherein the targeting hole comprises a targeting structure for receiving a targeting instrument.

17. The implant according to claim 1, wherein at least one hole has a central axis which is oblique relative to a vertical axis of the implant.

18. The implant according to claim 1, wherein the locking screw holes are adapted to receive cortical screws for fixing the implant to bone.

19. An implant system comprising
an implant with
a shaft region having one or more holes for receiving bone fasteners; and
a head region extending from the shaft region and having a plurality of circular holes for receiving bone fasteners, the plurality of circular holes including a central screw hole having a center and at least three locking screw holes each having a center and surrounding the central screw hole, wherein the centers of the locking screw holes define a polygon and wherein the center of the central screw hole is located on or within the polygon;
a compression screw adapted to be inserted into the central screw hole;
wherein the central screw hole comprises a part-spherical or conical hole portion on a side opposite the bone contacting surface;
at least three locking screws or cortical screws adapted for a locking engagement with the locking screw holes; and
a targeting hole located intermediate two of the locking screw holes, the targeting hole having grooves extending substantially radially therefrom on the side opposite the bone contacting side for stabilizing a targeting instrument.

20. The implant system according to claim 19, wherein each locking screw hole includes a locking structure adapted to lock a bone fastener to the implant.

21. The implant system according to claim 19, wherein the implant further comprises an oblong hole for receiving a further compression or locking screw.

22. The implant system according to claim 19, wherein the targeting hole comprises a targeting structure for receiving a targeting instrument.

23. A system comprising
an implant with
a shaft region having one or more holes for receiving bone fasteners; and
a head region extending from the shaft region and having a plurality of circular holes for receiving bone fasteners, the plurality of circular holes including a central screw hole having a center and at least three locking screw holes each having a center and surrounding the central screw hole, wherein the centers of the locking screw holes define a polygon and wherein the center of the central screw hole is located on or within the polygon
wherein the central screw hole comprises a part-spherical or conical hole portion on a side opposite the bone contacting surface;
a targeting instrument adapted to be secured to the implant;
wherein the head region of the implant further includes at least one targeting structure for receiving the targeting instrument, and wherein a portion of the targeting instrument is adapted to be fixedly secured to the targeting structure of the implant; and
wherein the targeting structure comprises a targeting hole located intermediate two of the locking screw holes and grooves extending substantially radially from the targeting hole for stabilizing the targeting instrument.

24. The system according to claim 23, wherein the head region of the implant further includes at least one targeting structure for receiving the targeting instrument, and wherein a portion of the targeting instrument is adapted to be fixedly secured to the targeting structure of the implant.

25. The system according to claim 23, wherein the targeting instrument includes a plurality of guide holes for guiding bone fasteners, drilling instruments or guiding instruments.

26. An implant, comprising:
a shaft region having one or more holes for receiving bone fasteners; and
a head region extending from an end of the shaft region and having five threaded locking screw holes for receiving bone fasteners having threaded heads, the five threaded holes surrounding an unthreaded central screw hole having a center and the five locking screw holes each having a center surrounding the unthreaded central screw hole, wherein the centers of the locking screw holes define a polygon and wherein the center of the unthreaded central screw hole is located on or within the polygon and further comprising a sixth threaded hole spaced from the central screw hole and located intermediate two of the threaded locking screw holes for receiving a targeting instrument, the implant having a bone-contacting surface and an opposite outwardly facing surface with the five threaded holes, the unthreaded central hole and the sixth threaded hole extending from the bone-contacting surface to the outwardly facing surface, the sixth threaded hole having grooves for positioning the targeting instrument extending radially outwardly therefrom along the outwardly facing surface.

* * * * *